United States Patent [19]

Bier

[11] Patent Number: 4,486,282
[45] Date of Patent: Dec. 4, 1984

[54] PRECIPITATION OF PROTEINS FROM SALT-CONTAINING PROTEINACEOUS FLUIDS EMPLOYING A DESALTING TREATMENT, AND USE THEREOF IN SELECTIVE PLASMAPHERESIS

[75] Inventor: Milan Bier, Tucson, Ariz.

[73] Assignee: University Patents, Inc., Norwalk, Conn.

[21] Appl. No.: 468,251

[22] Filed: Feb. 22, 1983

[51] Int. Cl.³ ................. B01D 13/02; B01D 13/00
[52] U.S. Cl. ................. 204/180 P; 204/301; 210/645; 210/257.2; 436/86; 422/48
[58] Field of Search ............ 204/180 P, 180 R, 301, 204/112 R, 112 B, 121, 122; 424/12, 36, 177, 96, 101; 23/902, 913, 915; 128/214 B, DIG. 22; 210/645–647, 257.2; 422/48; 436/86–89

[56] References Cited

U.S. PATENT DOCUMENTS 1,472,316  10/1923  Zeissler ..................... 424/177 X
4,216,205   8/1980  Radowitz ................... 424/101
4,276,140   6/1981  Jain .......................... 204/180 P
4,322,275   3/1982  Jain .......................... 204/180 P
4,351,710   9/1982  Jain .......................... 204/180 P Primary Examiner—John F. Niebling
Assistant Examiner—B. J. Boggs, Jr.
Attorney, Agent, or Firm—George M. Yahwak

[57] ABSTRACT

Total or fractional precipitation of proteins from salt-containing proteinaceous solution or suspension mixtures is induced or enhanced by subjecting the proteinaceous mixture to a desalting treatment, for example, by electrodialysis. In one aspect of the invention, the desalting treatment is used in conjunction with the addition of heavy metal ions to the proteinaceous mixture to provide a synergistic effect on the precipitation of the protein fraction. In another aspect of the invention, the desalting treatment, either with or without the heavy metal ion addition, is employed as an integral part of a selective plasmapheresis procedure for the removal or recovery of one or more selected plasma proteins from blood plasma.

28 Claims, 1 Drawing Figure

PRECIPITATION OF PROTEINS FROM SALT-CONTAINING PROTEINACEOUS FLUIDS EMPLOYING A DESALTING TREATMENT, AND USE THEREOF IN SELECTIVE PLASMAPHERESIS

BACKGROUND OF THE INVENTION

This invention relates to the fractionation of salt-containing proteinaceous solution or suspension mixtures by the total or fractional precipitation of their protein content and, more particularly, to the use of desalting techniques for inducing or enhancing such protein precipitation. Still more particularly, this invention is concerned with the use of such desalting techniques for effecting protein precipitation in combination with the addition of heavy metal ions and/or as an integral part of a selective plasmapheresis procedure for the removal or recovery of one or more selected plasma proteins from blood plasma.

It is well-known in the biochemical literature that the desalting of aqueous proteinaceous solution or suspension mixtures derived from biological fluids, i.e., the removal therefrom of the various salts and ions of alkali metals and alkaline earth metals normally present in such biological fluids, tends to cause precipitation of a protein fraction of variable and heterogeneous composition, generally known as euglobulins. A number of different techniques are well-known in the art for carrying out such desalting treatment, including, for example, passive dialysis, dilution, electrodialysis, ultrafiltration, and ion exchange chromatography. The fractionation of proteinaceous solution or suspension mixtures from biological fluids, including plasma, employing electrodialytic desalting, alone or in combination with other protein separation techniques, including forced-flow electrophoresis, electrodecantation, and alcohol precipitation, is described in the Stern U.S. Pat. No. 3,972,791, issued Aug. 3, 1976. However, this patent makes no mention whatsoever of using any desalting treatment either in combination with heavy metal ion precipitation of proteins, or as an integral part of a selective plasmapheresis procedure for the removal or recovery of one or more selected plasma proteins from blood plasma.

Heavy metal ions, such as zinc, ferrous, ferric, lead, silver, and mercury ions, are well-known in the art as exerting a precipitating action on proteinaceous materials by the reversible formation of insoluble metal-protein complexes. The use of heavy metal ions in protein precipitation and fractionation is reviewed in detail by Schultze and Heremans, "Molecular Biology of Human Proteins", Elsevier Publishing Co., New York, Vol. No. 1, pp. 259–261 (1966). The most commonly employed heavy metal ions, at least in regard to plasma protein fractionation, are zinc ions which, along with the iron-derived ions, are relatively nontoxic in comparison with the other heavy metal ions and, in fact, have beneficial nutritional effects in sufficiently limited doses. In the conventional plasma protein fractionation scheme using zinc ions for precipitating an immunoglobulin-rich fraction and leaving an immunoglobulin-impoverished albumin-rich supernatant fraction, the zinc ions are required in a concentration of 20 mM in decalcified plasma and 50 mM in citrated plasma (Pennell, R.B., in "Plasma Proteins", F.W. Putnam, Ed., Vol. I, Academic Press, 1960, p. 9). Even higher zinc ion concentrations are required for total precipitation of all proteins. Such high zinc ion concentrations in the resulting fractions must subsequently be removed, or at least significantly reduced, if such fractions are to be re-administered to human or animal recipients.

A widely used technique in the field of blood fractionation is plasmapheresis. In this technique, whole blood is withdrawn from a living donor, anticoagulated, and separated into a plasma fraction and a corpuscular element fraction, generally by centrifugation or filtration. In conventional plasmapheresis, the separated plasma fraction is retained, while the separated corpuscular element fraction is returned back into the blood stream of the donor. The primary use of plasmapheresis is the collection of plasma for subsequent preparation of purified plasma proteins employed in clinical medicine, without wasting the corpuscular elements of the donor's blood, for which there is little clinical demand. Approximately ten million plasmapheresis collections are carried out yearly in the United States for this purpose by commercial blood banks. From the plasma so-collected, only the few plasma proteins in greatest clinical demand, i.e., antihemophilia Factor VIII, immunoglobulin IgG, and serum albumin, are generally recovered, with all of the other numerous plasma proteins being mostly wasted.

In addition to its use in the preparation of clinically useful, purified plasma proteins, plasmapheresis has recently been gaining increasing attention as a modality for the direct treatment of a variety of diseases. The purpose of such therapeutic plasmapheresis is the removal from the patient's blood of pathologic plasma proteins or plasma proteins which are present in a noxiously high concentration. A variety of diseases may involve such noxious proteins. Best known among these are the gammopathies, multiple myeloma, and Waldenstrom's macroglobulinemia. The increased concentration of abnormal monoclonal immunoglobulins in the plasma of these patients may cause life-threatening hyperviscosity of the blood. Another category of diseases containing abnormal proteins are the autoimmune diseases, such as lupus erythematosus, myasthenia gravis, and, possibly, arthritis and cancer, where the primary offending components of the plasma are either specific antibodies or circulating antigen-antibody complexes. A third category of diseases may be considered as having genetically determined errors in metabolism, as for instance, homozygous familial hypercholesterolemia, characterized by abnormally high levels of circulating lipoproteins. As a treatment for these various categories of diseases, therapeutic plasmapheresis has been found to cause not only short-term palliative amelioration, but also, in certain cases, to cause long-term improvements.

In conventional plasmapheresis, whether carried out for preparative purposes or for therapeutic purposes, all of the plasma components are withdrawn from the donor's circulation, even though the main objective is the recovery or removal of not more than a few selected plasma proteins. The chief drawback of this procedure is that only a limited volume of plasma can be drawn from a given donor, if no plasma replacement is given. For more intensive treatments, the withdrawn plasma must be replaced either with purified albumin, or with normal plasma or other suitable plasma replacement fluid. This latter form of treatment is referred to as plasma exchange. Purified albumin is very expensive and does not provide all the proteins necessary for optimal replacement. Replacement with normal plasma is also expensive, and carries the risk of hepatitis. Moreover, the supply of normal plasma may soon be insufficient to fulfill the needs of all the patients who may benefit from such treatment.

In order to overcome these shortcomings of conventionaly plasmapheresis, attempts have been made to develop selective plasmapheresis techniques for selectively removing only the clinically useful or noxious plasma proteins while leaving the bulk of the remainder of the plasma components in the donor's circulation, thereby enabling extensive plasmapheresis without the need for any plasma replacement. In these selective plasmapheresis techniques, the plasma fraction, after being separated from the corpuscular element fraction, is treated so as to remove one or more selected plasma proteins therefrom, and the resulting protein-impoverished plasma fraction is thereafter recombined with the corpuscular element fraction for return back into the donor's bloodstream. In one such system, described, for example, by Terman, et al., *FEBS Letters,* Vol. 68, No. 1, pp. 89–94 (September, 1976), the protein-impoverished plasma fraction is obtained by passing the plasma fraction through an immunoadsorption column to cause adsorption of certain immunoglobulins and/or immune complexes. This technique offers a high degree of specificity in the profile of proteins removed, but as an on-line technique for treating plasma maintained in extracorporeal circulation during a continuous or semi-continuous flow plasmapheresis procedure, it has a rather limited potential for withdrawing large quantities of immunoglobulins from the plasma due to the limited binding capacity of the immunoadsorption column. In another selective plasmapheresis technique previously developed by the present inventor, forced-flow electrophoresis is employed for separating an immunoglobulin-rich fraction from plasma on the basis of differences in electrophoretic mobility. Bier, et al., *Trans. Amer. Soc. Artif. Int. Organs,* Vol. 16, pp. 325–333 (1970). While this technique offers the potential of withdrawing large quantities of immunoglobulins and the additional advantage of yielding them in a readily accessible form, forced-flow electrophoresis is rather time-consuming and cumbersome to implement as an on-line technique for treating plasma maintained in extracorporeal circulation during a continous or semi-continuous flow plasmapheresis procedure. It should be noted that neither one of these two previously proposed selective plasmapheresis techniques involves the separation of proteins based upon their differences in solubility.

SUMMARY OF THE INVENTION

It is, accordingly, a primary object of the present invention to provide new and improved techniques for the fractionation of salt-containing proteinaceous solution or suspension mixtures, involving the total or fractional precipitation of their protein content.

Another object of the invention is to provide a fractionation technique in accordance with the preceding object, which involves a heavy metal ion precipitation of the protein fraction, and which enables a reduction in the heavy metal ion concentration required for effecting such precipitation.

A further object of the invention is to provide a fractionation technique in accordance with the preceding object, which eliminates the need for removal, or facilitates the recovery of, the added heavy metal ions from the resulting fractions.

Another object of the invention is to provide a fractionation technique in accordance with the preceding object, which enables a reduction in the amounts of acid or base needed for adjustment of the pH of the proteinaceous mixture for maximizing the protein precipitation.

Still another object of the invention is to provide a new and improved selective plasmapheresis technique for the removal or recovery of one or more selected plasma proteins from whole blood, which involves a controllable preferential precipitation of said selected plasma proteins from the separated plasma fraction.

A still further object of the invention is to provide a selective plasmapheresis technique in accordance with the preceding object, which enables a modulation of the protein profile of the precipitated protein fraction so as to provide flexibility in the use of the technique for both preparative and therapeutic purposes.

Yet another object of the invention is to provide a selective plasmapheresis technique in accordance with the preceding object, which is capable of relatively rapidly and conveniently effecting an on-line withdrawal of said selected plasma proteins in relatively large quantities and in a readily accessible form from plasma maintained in extracorporeal circulation during a continuous or semicontinuous flow plasmapheresis procedure.

A yet further object of the invention is to provide a continuous or semicontinuous flow selective plasmapheresis apparatus for carrying out an on-line selective plasmapheresis technique in accordance with the preceding object.

The above and other objects are achieved in accordance with the present invention which, in each of its aspects, involves the fractionation of a proteinaceous solution or suspension mixture derived from a biological fluid and containing one or more salts selected from the group consisting of alkali metal salts and alkaline earth metal salts, by precipitation of a protein fraction therefrom, and subsequent separation of the precipitated protein fraction from the supernatant protein-impoverished mixture, and wherein such protein precipitation is either induced or enhanced by subjecting the proteinaceous mixture to a desalting treatment controlled so as to reduce the salt content thereof to a predetermined level.

In one aspect of the invention, the desalting treatment is employed in combination with the incorporation into the proteinaceous mixture, either prior or subsequent to the desalting treatment, of a predetermined concentration of heavy metal ions. It has unexpectedly been discovered that these two known protein precipitation-inducing techniques, when utilized in combination with each other, not only have an enhancing effect upon each other but also are capable of cooperating to provide a synergistic precipitation of a protein fraction from the resulting heavy metal ion-containing desalted mixture. In this regard, it should be noted that by the term "synergistic precipitation", as employed herein throughout the specification and in the appended claims, it is intended to denote a total precipitating effect which is greater than the sum of the precipitating effects, when taken independently, of: (1) the extent of desalting employed, i.e., the predetermined level to which the salt content of the proteinaceous mixture is reduced by the desalting treatment; and (2) the predetermined concentration of heavy metal ions employed. In carrying out this aspect of the invention, such predetermined level of salt content and such predetermined concentration of heavy metal ions are each selected and coordinated so that the combination thereof provides such synergistic precipitation of the protein fraction.

This aspect of the invention constitutes a significant improvement over the heavy metal ion precipitation procedures previously employed for the fractionation of proteinaceous solution or suspension mixtures derived from naturally occurring biological fluids, in significantly reducing the heavy metal ion concentration required for effecting precipitation of a given protein fraction. This feature is particularly advantageous in the fractionation of plasma or serum proteins with heavy metal ions which are nontoxic in sufficiently low doses (i.e., zinc, ferric, and ferrous ions), where the recovered fractions are to be re-administered to human or animal recipients. By sufficiently reducing the concentration of these heavy metal ions needed to cause precipitation of the desired protein fraction, the need to remove these ions from the resulting fractions is minimized or even completely avoided. Furthermore, where the removal or recovery of the added heavy metal ions from the resulting fractions is necessary or desirable, for example, for the reuse of the recovered heavy metal ions in further precipitation, such removal or recovery of the heavy metal ions is facilitated by the absence of the originally present background salts which have been removed during the desalting treatment.

In another aspect of the invention, the desalting treatment, either without or in combination with heavy metal ion addition, is employed as an integral part of a selective plasmapheresis technique for the removal or the recovery of one or more selected plasma proteins from whole blood. The selective plasmapheresis procedure is carried out by withdrawing whole blood from a living donor and separating the whole blood into a plasma fraction and a corpuscular element fraction, in the conventional manner. The separated plasma fraction is then subjected to a desalting treatment controlled so as to reduce the physiological salt content thereof to a predetermined level at which the selected plasma proteins will preferentially precipitate. The desalting treatment may optionally be carried out in conjunction with the addition to the plasma of relatively nontoxic heavy metal ions, such as zinc, ferric, and ferrous ions, in a concentration sufficient to enhance the preferential precipitation of the selected plasma proteins. After separating the precipitated protein fraction, the salt balance of the remaining supernatant protein-impoverished desalted plasma fraction is reconstituted back to a physiological level. The resulting salt-reconstituted protein-impoverished plasma fraction is thereafter recombined with the corpuscular element fraction, and the recombined fractions are then returned back into the bloodstream of the donor, in the conventional manner.

The selective plasmapheresis technique in accordance with the present invention enables a modulation of the protein profile of the precipitated protein fraction by controlled variations in the extent of desalting and pH conditions, and by the optional addition of a precipitation-enhancing concentration of heavy metal ions. Such modulation feature provides the technique with substantial flexibility and versatility so as to enable its utilization both for preparative purposes in the recovery of clinically useful plasma proteins, as well as for therapeutic purposes in effecting a therapeutically effective removal of noxious plasma proteins from a patient's blood. Furthermore, the technique is capable of relatively rapidly and conveniently effecting an on-line withdrawal of the selected plasma proteins in relatively large quantities and in a readily accessible form from plasma maintained in extracorporeal circulation in a continuous or semicontinuous flow plasmapheresis system.

Such continuous or semicontinuous flow selective plasmapheresis system may be readily implemented in accordance with the present invention by incorporating on-line with conventional continuous or semicontinuous flow plasmapheresis apparatus a suitable combination of standard commercially available desalting, precipitate separating, and salt balance reconstituting equipment, such as, for example, an electrodialyzer, a centrifuge or filter, and a passive dialyzer, respectively.

BRIEF DESCRIPTION OF THE DRAWINGS

The selective plasmapheresis aspect of the present invention is illustrated in the accompanying drawings, wherein.

DESCRIPTION OF PREFERRED EMBODIMENTS

Figure 1:
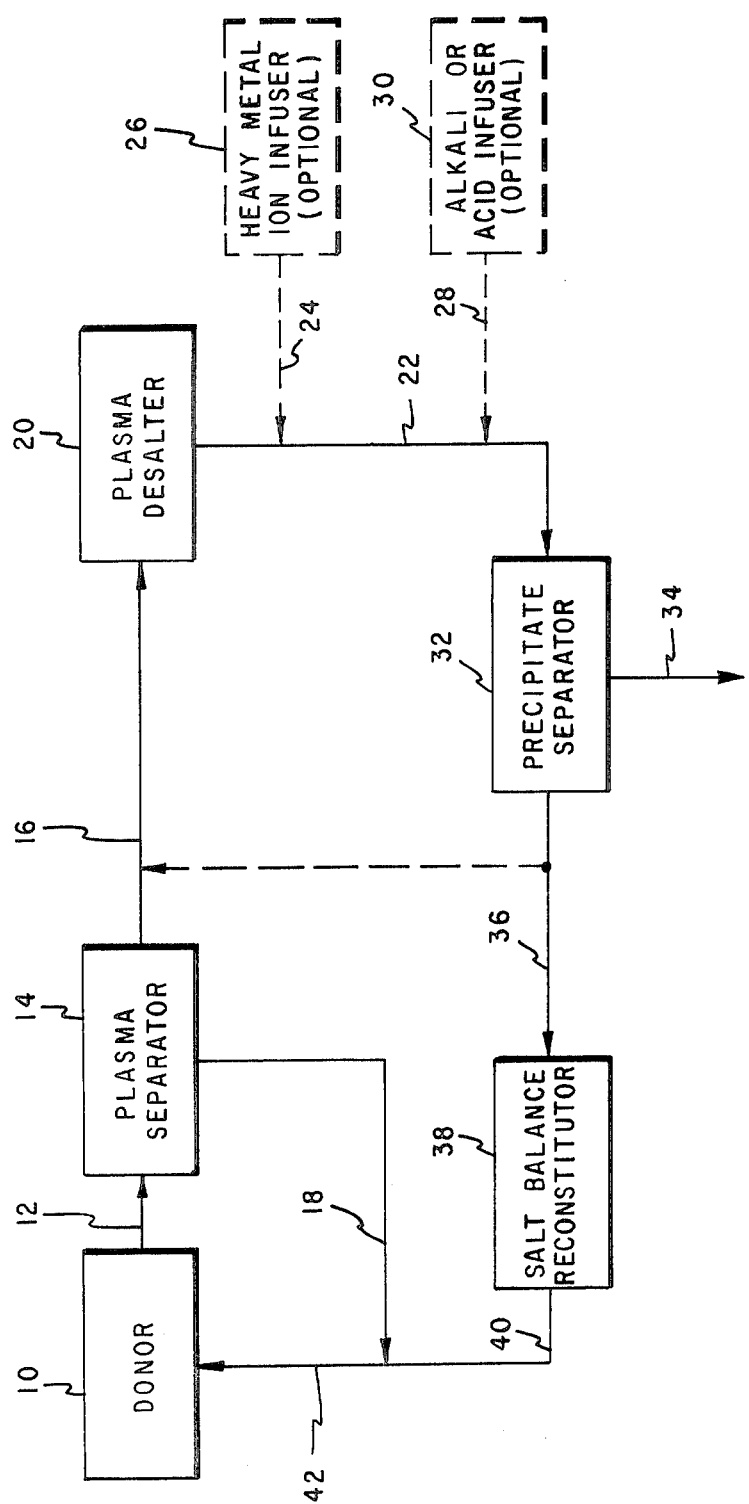
FIG. 1 is a schematic flow diagram showing the preferred sequence of steps and equipment utilized in the continuous or semicontinuous flow selective plasmapheresis system in accordance with the present invention.

The desalting treatment employed in each of the aspects of the present invention can be carried out by any one of the various desalting techniques well-known in the art including, for example, electrodialysis, dilution, passive dialysis, ion exchange chromatography, and ultrafiltration. Of these various desalting techniques, the most efficient and versatile, particularly when a high degree of desalting is desired, is electrodialysis, which has been developed specifically for optimizing the removal of salts from aqueous solutions or suspensions. Electrodialysis is an electrical desalting process based on the use of ion-selective membranes. It was originally developed for the desalting of saline waters, but has received a variety of other industrial applications, particularly for the desalting of milk whey (as described in U.S. Pat. Nos. 3,433,726; 3,447,930; 3,595,766; 3,757,005; and 3,754,650), and in the fractionation of proteins (as described in U.S. Pat. No. 3,972,791).

In a common configuration, an electrodialyzer is constituted by a parallel array of alternating anion and cation perm-selective membranes, with a d.c. electric current applied across said array. The solution to be desalted circulates through every second compartment defined by the membranes, and a saline brine solution circulates through the alternate compartments and receives the salts from the solution being desalted. The rate of fluid flow through the compartments has to be rather high, to minimize concentration polarization along the membranes.

Electrodialysis can be carried out in either a continuous mode, a recirculating mode, or a recirculating-continuous mode, this latter mode sometimes being referred to as a feed-and-bleed mode. When a single pass through the electrodialyzer is sufficient to cause the desired degree of desalting, the continuous mode will be employed. When a higher degree of desalting is desired, it is necessary to operate in one of the other two modes. In the recirculating mode, the electrodialysis is carried out as a batch process, a given batch of fluid being recirculated until the desired degree of desalting is obtained. The recirculating-continuous mode is a combination of the other two modes, enabling a high degree of desalting with a continuous fluid flow. In this latter mode, a small batch of fluid is continuously recycled through the electrodialyzer, and a small portion of the recirculating fluid is continuously withdrawn at the desired degree of desalting, this fluid being continuously replaced by the addition of fresh fluid to be desalted.

While electrodialytic desalting is preferred for use in the present invention, the various other desalting techniques listed above, at least in some applications, may suitably be used in place thereof. The quickest and simplest technique for reducing the salt content of a fluid is simple dilution, but its drawback is that it results in greatly increased volumes. Passive dialysis, which is quite effective in equilibrating salt concentrations across a semi-permeable membrane and hence extensively used in artificial kidneys for hemodialysis, is not well suited for extensive desalting, since large volumes of salt-free dialysate are necessary to reduce the salt content of the processed fluid. Ion exchange chromatography, which is extensively used for the desalting of various fluids, such as sugar solutions, is somewhat less efficient than electrodialysis for the desalting of some of these fluids, such as plasma or milk whey, as it is more difficult to carry out the process in a sanitary manner, the proteins also binding with the ion exchange resins. Ultrafiltration, which utilizes controlled porosity membranes for the separation of high molecular weight proteins from lower molecular weight salts and carbohydrates, differs from electrodialysis mainly in the fact that it does not readily separate low molecular weight carbohydrates from salts.

Regardless of which of the above-described desalting techniques is employed in carrying out the present invention, the extent of desalting may be readily monitored and controlled by measurement of the specific resistance of the solution being desalted, for example, by means of an in-line conductivity measuring cell. As the salt content of the solution becomes reduced, the specific resistance of the desalted solution will gradually increase. The exact extent of desalting necessary to achieve the desired effects in accordance with the present invention will vary over a rather broad range, for example, to a final salt content level corresponding to a specific resistance ranging from about 300 to greater than 100,000 ohm-cm, depending upon which aspect of the invention is being practiced and the desired protein profile of the protein fraction to be precipitated.

When the desalting treatment is employed for reducing the concentration of heavy metal ions required for effecting precipitation of a given protein fraction, the more extensive the desalting treatment, the more pronounced will be its enhancing effect. As a general rule, it is desirable for this purpose to desalt the proteinaceous solution being fractionated to a level at which the resulting desalted solution exhibits a specific resistance greater than 300 ohm-cm, preferably greater than 10,000 ohm-cm, and in some instances, to carry out an exhaustive desalting to a specific resistance greater than 100,000 ohm-cm.

The heavy metal ions used in the practice of the present invention are those which are well-known in the art to exert a precipitating action on proteinaceous materials and include, for example, zinc, ferrous, ferric, lead, silver, and mercury ions. Zinc and the iron-derived ions are the preferred metal ions, since they are relatively nontoxic and, in sufficiently small doses, have a beneficial nutritional effect. The heavy metal ions are conveniently used in the present invention in the form of aqueous solutions of any of their commonly available salts such as, for example, chlorides, sulfates, citrates, glycinates, and the like. The particular salt employed has no substantial effect upon the amount of heavy metal ions required for the protein precipitation.

For each of the various heavy metal ions which may be employed in the practice of the present invention, there is generally a relatively narrow pH range at which its protein-precipitating action is optimal. For example, the protein-precipitating action of zinc ions is optimal in the pH range of from about 6.5 to about 8, particularly from 7 to 7.5, while that of ferric ions is optimal in the pH range of from about 4 to about 5. If necessary for adjusting the pH of the proteinaceous mixture being treated to a value within the range which is optimal for the protein-precipitating action of the heavy metal ions employed, the heavy metal ion addition is advantageously accompanied by a pH adjustment step with an appropriate amount of an alkali or acid solution, preferably added separately from the heavy metal ion solution to avoid any metal hydroxide precipitation. Such solutions should be added to the proteinaceous mixture being treated with strong mixing or stirring to avoid local concentration build-up. Such methods of administration are common practice in addition of any reagents to protein solutions. It is possible to add these reagents either to a batch of proteinaceous mixture or to a flowing stream thereof, the rate of addition being kept in the desired proportion to the rate of proteinaceous mixture flow.

The incorporation of the heavy metal ions, and any alkali or acid which may be necessary for pH adjustment, into the proteinaceous mixture being fractionated, may be carried out either prior or subsequent to the desalting treatment. A synergistic precipitation of the protein fraction from the proteinaceous mixture is obtainable with either one of these two sequences of operation. However, there are certain differences which exist between the two protocols which may make one more advantageous than the other in certain protein fractionation applications. Carrying out the desalting treatment prior to the heavy metal ion addition offers the advantage of requiring a heavy metal ion concentration which is approximately an order of magnitude less than that required for effecting the same degree of precipitation with the reverse sequence. Hence, this is the protocol which should be followed if the primary consideration is to obtain an optimal reduction in the heavy metal ion concentration required for effecting the precipitation. On the other hand, the reverse sequence offers the advantage of enabling removal of the excess heavy metal ions from the proteinaceous mixture simultaneously with the desalting treatment, thereby eliminating any need for any subsequent further treatment for this purpose.

The precise concentration of heavy metal ions which will be required in conjunction with the desalting treatment for effecting the synergistic protein precipitation in accordance with the present invention, will vary considerably depending upon a number of factors, including the particular heavy metal ions employed, the composition and pH of the proteinaceous mixture being fractionated, the desired protein profile of the precipitated protein fraction, the extent of desalting employed, and the sequence in which the desalting treatment and the heavy metal ion addition are carried out. In any given proteinaceous mixture fractionation system and scheme within the scope of the present invention, the heavy metal ion concentration and the extent of desalting employed can be selected and coordinated so that the combination thereof provides a synergistic precipitation of the desired protein fraction from the resulting heavy metal ion-containing desalted mixture. In any event, the heavy metal ion concentration employed will be considerably less, e.g., from about ½ to about 1/25, than that which would be required for effecting the comparable precipitation in the absence of the desalting treatment. By way of example, in the absence of any desalting treatment, a zinc ion concentration of 50 mM is required for effecting precipitation from citrated human plasma of an immunoglobulin-rich fraction, leaving an immunoglobulin-impoverished albumin-rich fraction as the supernatant. When this same fractionation is carried out in accordance with the present invention, with the zinc ion addition being preceded by a desalting of the citrated plasma to a specific resistance of about 50,000 ohm-cm or higher, the required zinc ion concentration is reduced to a value of from about 2.5 to about 4 mM. Similarly, in the absence of a desalting treatment, a zinc ion concentration ranging from 43 to 60 mM is required for effecting complete protein precipitation from sweet milk whey. When this same fractionation is carried out in accordance with the present invention, with the zinc ion addition being preceded by a desalting of the whey to specific resistances of 2,000 and 20,000 ohm-cm, the required zinc ion concentration is reduced to 20 mM and 7 mM, respectively.

While not intending to be limited by any particular theory of the mechanism of action involved in the present invention, it would appear that the variety of salts and ions normally present at physiological levels in naturally occurring biological fluids, including the usual metallic ions of sodium, potassium, calcium, magnesium, etc., tend to interfere with the heavy metal ion precipitation of proteins from their solutions or suspensions, presumably by competing with the heavy metal ions for the negatively charged binding sites on the protein surface. The reduction in the level of these background salts resulting from the desalting treatment employed in the present invention, apparently eliminates or at least substantially reduces such interfering effect, thereby substantially increasing the protein-precipitating efficiency of the heavy metal ions. This is in direct contrast with other types of protein-precipitating reagents, for example, ammonium sulfate, whose protein-precipitating action is enhanced by the presence of sodium chloride.

Employing a desalting treatment in combination with heavy metal ion precipitation of proteins in accordance with the present invention, also tends to decrease the quantity of alkali or acid which may be needed for adjusting the pH of the proteinaceous mixture to a value within the range which is optimal for the protein-precipitating action of the heavy metal ions. The quantity of alkali or acid needed for this pH adjustment may be smaller in desalted mixtures than in nondesalted mixtures, because some of the buffering ions in the original proteinaceous mixture have been removed. In addition, less alkali or acid may be needed to compensate for the buffering action of the heavy metal ions themselves.

Separation of the precipitated protein fraction from the supernatant protein-impoverished mixture may be suitably carried out by conventional centrifugation or filtration, with or without prior settling. Thereafter, if necessary or desired, the heavy metal ions added during the fractionation may be removed or recovered from one or both of the precipitated protein fraction and the supernatant mixture.

Particularly where the heavy metal ions employed are relatively nontoxic (i.e., zinc, ferric, and ferrous ions), their reduced concentration employed in the fractionation technique of the present invention will generally minimize or even completely avoid the necessity for removing these ions from the recovered fractions, even where the recovered fractions are to be re-administered to human or animal recipients. Such removal or recovery of the heavy metal ions, as well as the alkali or acid employed for pH adjustment, may, nevertheless, be advantageous in certain cases. For example, it might be desirable to reduce the cost of the precipitation by reusing the recovered heavy metal ions and alkali or acid in further precipitation. Such recycling offers the further benefit of avoiding any environmental pollution which might result from the discharge of the precipitating heavy metal ions into waste streams.

Removal or recovery of the heavy metal ions and the alkali or acid can be easily accomplished by subjecting the resulting fractions, after separation, to electrodialysis or one of the other desalting processes listed above. Such removal or recovery is facilitated by the absence of the originally present background salts which have been removed during the prior desalting treatment. For treating the precipitated protein fraction in this manner, it can be first resuspended by agitation and totally or partially resolubilized, for example, by addition of salts, such as sodium chloride, by readjustment of the pH to a value outside its optimal precipitation range, and/or by addition of a metal ion chelating agent.

The fractionation technique in accordance with the present invention, employing a desalting treatment in combination with heavy metal ion addition, has a variety of applications in the fractionation of various salt-containing proteinaceous solution or suspension mixtures. Its simplest application is in the total recovery of all proteins present in such proteinaceous mixtures, where the reduction in the concentration of heavy metal ions needed to cause precipitation, as well as the facilitated recycling of the heavy metal ions, may significantly reduce the cost of the process. Primary examples of such proteinaceous mixtures, whose fractionation can be enhanced in this manner, are blood plasma, serum, and fractions derived therefrom, and milk whey, all of which have a rather high salt content. The technique may also be applicable to the recovery of proteins from proteinaceous mixtures obtained as a by-product of a variety of industrial operations, such as the preparation of processed foods from potatoes, grain, fish, meat, and the like. The recovery of the proteins from such proteinaceous mixtures may not only be economically advantageous, but may also alleviate the serious water pollution problem caused by protein-containing waste. In addition, increasing attention is being given to the recovery of proteins from sources not normally used in human or animal nutrition, such as leaves, grasses, cornhusks, algae, bacteria, and many agricultural waste products.

With many proteinaceous mixtures, the technique is also applicable to the recovery of purified carbohydrates, remaining in the supernatant after precipitation of the protein fraction. This is the case, for instance, with milk whey, which contains only about 0.5–0.8% of protein, but 4–5% of lactose sugar.

In addition to the total recovery of all proteins present in a proteinaceous mixture, the present fractionation technique is also applicable for separating the proteinaceous mixture into two different protein-containing fractions. As a rule, globulins are precipitated at lower heavy metal ion concentrations than is albumin. This is of particular importance in blood plasma fractionation, but may also be applicable to other protein systems, such as in the separation of lactoglobulin and whey immunoglobulins from lactalbumin. In the case of blood plasma fracionation, this fractional precipitation technique can yield an immunoglobulin-rich fraction as the precipitated protein fraction, and an immunoglobulin-impoverished albumin-rich fraction as the supernatant. The immunoglobulin-rich fraction may be used as a source for the preparation of purified immunoglobulins, while the immunoglobulin-impoverished albumin-rich fraction may be used as a plasma replacement in therapeutic plasmapheresis or plasma exchange, or as nutrient factors in tissue culture. As an example of the rationale for the potential use of the immunoglobulin-impoverished albumin-rich fraction in tissue culture, it may be sufficient to cite the frequent requirement for fetal or new-born calf serum as a growth factor in tissue culture, the antibodies present in adult bovine serum or plasma having a deleterious effect on the tissue culture.

By way of example, the fractionation technique of the present invention has been found to be particularly useful for precipitating an immunoglobulin-rich fraction from blood plasma, and leaving an immunoglobulin-impoverished albumin-rich fraction as the supernatant. Specifically, when citrated plasma is first desalted to a specific resistance of over 10,000 ohm-cm, and then zinc ions are added to the desalted plasma in a concentration of from about 2.5 to about 4 mM, followed by pH adjustment to about pH 7 by the addition of sodium hydroxide solution, the resulting precipitated fraction contains approximately 80% of the original plasma IgG value, while the resulting supernatant fraction contains approximately 80% of the original plasma albumin value. In comparison, the desalting treatment alone, without the addition of zinc ions, causes the precipitation of only about 20% of the original plasma immunoglobulin IgG value.

These aspects of the invention bear direct relation to the commercial fractionation of pooled plasma. Schultze and Heremans (op. cit.) and Pennell (op. cit.) have both summarized the state of art of commercial plasma fractionation with particular reference to the use of zinc and other heavy metal ions. The present discovery of the synergistic action of desalting and heavy metal ions may significantly reduce the cost of commercial plasma fractionation and present other advantages in terms of purity and yield of the fractionation process.

The plasma protein-precipitating action of the desalting treatment, and its ability to be enhanced by the addition of low concentrations of heavy metal ions, are utilized in accordance with the present invention as an integral part of a selective plasmapheresis technique for the removal or recovery of one or more selected plasma proteins from whole blood. In this aspect of the invention, the addition of a precipitation-enhancing concentration of heavy metal ions is employed as an optional step which, together with controlled variations in the extent of desalting and pH conditions, serves to modulate the protein profile of the precipitated protein fraction resulting from the desalting treatment.

In selective plasmapheresis procedures, in general, the primary objective is to effect a preferential removal from the separated plasma fraction of one or more selected plasma proteins, while leaving the bulk of the remaining plasma components in a form suitable for re-administration to the donor. Such selected plasma proteins, whose preferential removal is desired, are either the clinically useful plasma proteins, such as immunoglobulin IgG and Factor VIII, when the procedure is carried out for preparative purposes; or noxious plasma proteins, including various immunoglobulins, macroglobulins, antibodies, antigen-antibody complexes, and lipoproteins, when the procedure is carried out for therapeutic purposes. The selective plasmapheresis technique in accordance with the present invention is based upon the discovery that a combination of circumstances exist which render a desalting treatment, either alone or in combination with heavy metal ion addition, particularly suitable for use in selective plasmapheresis. Firstly, all of the various selected plasma proteins enumerated above either are euglobulins, and hence automatically precipitatable upon suitable reduction of the physiological salt content of the plasma; or are precipitatable by means of such desalting treatment in combination with the addition of a low concentration of heavy metal ions to the plasma. Secondly, a preferential precipitation among these various selected plasma proteins can be achieved by certain factors which modulate the protein profile of the precipitated protein fraction, these modulating factors being controlled variations in the extent of desalting and pH conditions, and the optional addition of a precipitation-enhancing concentration of heavy metal ions. Thirdly, after separation of the precipitated protein fraction, the supernatant protein-impoverished desalted plasma fraction can be rendered suitable for re-administration to the donor by reconstituting its salt balance back to a physiological level. The combination of these three circumstances form the basis for the selective plasmapheresis technique in accordance with the present invention.

In carrying out the selective plasmapheresis procedure in accordance with the present invention, whole blood is first withdrawn from a living donor and separated into a plasma fraction and a corpuscular element fraction, by the procedures commonly used in conventional plasmapheresis and well-known in the art. For example, a batch method of manual plasmapheresis can be employed for this purpose, wherein whole blood is collected in a specially designed plastic collection bag containing an anticoagulant. This bag is centrifuged, and the supernatant plasma is gently expelled into a second bag, while the packed corpuscular elements are returned to the donor with the addition of physiologic saline. Alternatively, the so-called machine plasmapheresis method can be employed, wherein the donor's blood supply is directly connected to a continuous or semicontinuous flow centrifuge, from which a flow of plasma is obtained. In the continuous flow centrifuges, there is also a continuous return flow of the packed cells; while in the semicontinuous flow centrifuges, plasma flow has to be interrupted during the return of the packed cells. Such centrifuges are commercially available from the Aminco Division of Baxter Laboratories, the Haemonetics Corporation, and others. As a further alternative, filtration plasmapheresis can be used, in which whole blood is recycled through a crossflow membrane filter, to yield a continuous flow of plasma and continuous return of the corpuscular elements to the donor.

The separated plasma fraction is then subjected to a desalting treatment controlled so as to reduce the physiological salt content thereof to a predetermined level at which the plasma proteins whose removal is desired will preferentially precipitate. While the desalting treatment suitably may be effected using any one of the various conventional desalting techniques described above, electrodialytic desalting is the most efficient and hence is the method of choice. The extent of desalting can be monitored and controlled by continuous measurement of the specific resistance of the plasma by means of an in-line conductivity measuring cell. In addition, the current output of the power supply of the electrodialyzer continuously decreases as the resistance of the electrodialyzed plasma increases and serves as an additional control.

The protein profile of the precipitated protein fraction will generally include one or more plasma proteins selected from the group consisting of immunglobulins, macroglobulins, antibodies, antigen-antibody complexes, lipoproteins, and Factor VIII, depending upon whether the selective plasmapheresis is being carried out for the preparation of clinically useful plasma proteins or for the therapeutic removal of noxious plasma proteins. Such protein profile may be effectively modulated by controlled variations in the extent of desalting and pH conditions, and by the optional addition to the plasma fraction of relatively nontoxic heavy metal ions, such as zinc, ferric, and ferrous ions, in a concentration sufficient to enhance the preferential precipitation of the desired plasma proteins. By way of example, macroglobulins begin to precipitate at a salt content level corresponding to a specific resistance of 300 ohm-cm; antigen-antibody immune complexes begin to precipitate at a salt content level corresponding to a specific resistance of 700 ohm-cm; and other human plasma proteins begin to precipitate at a salt content level corresponding to a specific resistance of 1000 ohm-cm. Furthermore, while immunoglobulin IgG will be precipitated in small amounts (about 20% of the original plasma value) by desalting alone, such precipitation may be enhanced to about 80% of the original plasma value by the addition to the previously desalted plasma of zinc ions in a concentration of from about 2.5 to about 4 mM. When heavy metal ion addition is employed, such ions are preferably added subsequent to the desalting treatment. When added prior to the desalting treatment, a higher concentration of the heavy metal ions will be required. For example, for obtaining a precipitation enhancing effect similar to that described above, the required concentration of zinc ions when added to the plasma prior to the desalting treatment, is from about 15 to about 25 mM. The desalting treatment will generally simultaneously result in the reduction of the pH of the plasma to the average isoelectric point of the plasma proteins. The heavy metal ion addition should, if necessary, be accompanied by an adjustment of the pH of the plasma to a value within the range which is optimal for the protein-precipitating action of the heavy metal ions employed. For example, with zinc ions, such range is from about 6.5 to about 8.

The precipitated protein fraction is then separated from the supernatant protein-impoverished desalted plasma fraction in one of three different ways, corresponding essentially to the means employed in separating the plasma fraction from the corpuscular element fraction, i.e., by batch centrifugation, using the plastic bags in which plasma is obtained from manual plasmapheresis; by continuous centrifugation, using centrifuges essentially similar to those used for machine plasmapheresis; or by filtration. If the plasma is obtained by machine plasmapheresis, and continuous centrifugation is employed for separating the precipitated protein fraction, then two rotors are necessary to carry out the procedure in a continuous manner. If filtration is employed for separating the precipitated protein fraction, the filters used should not be of the type used in filtration plasmapheresis, i.e., membrane filters, as they have but small capacity for precipitate retention. Instead, these filters should be indepth fiber filters of the type used for blood filtration, as for instance, the Swank transfusion filter, available from Extracorporeal Medical Specialties, Inc. If either continuous centrifugation or filtration is employed for separating the precipitated protein fraction, it can be employed separately from the desalting step, or, alternatively, it can be made an integral part of the desalting step, the plasma circulating in a continuous path through both the electrodialyzer and the precipitate separating device.

After separating the precipitated protein fraction, the salt balance of the remaining supernatant protein-impoverished desalted plasma fraction is reconstituted back to a physiological level. This can be accomplished in one of two manners. In the preferred procedure, the salt balance reconstitution step is carried out by passive dialysis of the protein-impoverished desalted plasma fraction against a suitable physiologically balanced electrolyte solution, using artificial kidneys or other passive dialyzers. Single pass flow or recirculation can be employed, and the dialysate is essentially similar to that employed in hemodialysis. In this procedure, there is no need to know the ionic composition of the desalted plasma, since salt balance reconstitution is automatic. The progress of the salt balance reconstitution can be monitored by conductivity measurement of the returning plasma.

In an alternative method, the salt balance reconstitution step may be carried out by the addition of a concentrated solution of suitably balanced electrolytes to the protein-impoverished desalted plasma fraction. Such concentrated solutions are commercially available for the preparation of dialysate used in hemodialysis. In this procedure, it is necessary to know the extent of desalting to which the plasma has been submitted, i.e., the quantity of concentrate has to be geared to the amount of desalting. Conductivity monitoring or specific ion concentration monitoring can be employed to ascertain the degree of salt balance reconstitution. When desalting has been carried out to a sufficient degree that virtually all of the original plasma salts have been removed (i.e., when the plasma resistance has been increased by a factor of ten or more, corresponding to the removal of 90% or more of salts), then the reconstitution of all normal electrolytes is required.

The resulting salt-reconstituted protein-impoverished plasma fraction is thereafter recombined with the corpuscular element fraction, and the recombined fractions are then returned back into the bloodstream of the donor, in the conventional manner known in the art.

The ability to modulate the protein profile of the precipitated protein fraction by controlled variations in the extent of desalting and pH conditions, and by the optional addition of a precipitation-enhancing concentration of heavy metal ions, provides the selective plasmapheresis technique of the present invention with substantial flexibility and versatility so as to enable its utilization both for preparative purposes in the recovery of clinically useful plasma proteins, as well as for therapeutic purposes. By way of example of its use for preparative purposes, the selective plasmapheresis technique can yield an immunoglobulin-rich fraction as the precipitated protein fraction, leaving an immunoglobulin-impoverished albumin-rich fraction as the protein-impoverished plasma fraction. The immunoglobulin-rich fraction may be used as a source for the preparation of purified immunoglobulins. When used for therapeutic purposes in the treatment of a patient whose circulating blood contains a noxiously high concentration of immunoglobulins, macroglobulins, antibodies, antigen-antibody complexes, and/or lipoproteins, the selective plasmapheresis procedure can be carried out to an extent sufficient to provide a therapeutically effective removal of the noxious proteins from the patient's circulating blood.

The selective plasmapheresis technique of the present invention, furthermore, is capable of relatively rapidly and conveniently effecting an on-line withdrawal of the selected plasma proteins in relatively large quantities and in a readily accessible form from plasma maintained in extracorporeal circulation in a continuous or semi-continuous flow selective plasmapheresis system. The preferred sequence of steps and equipment utilized in such a continuous or semicontinuous flow selective plasmapheresis system in accordance with the present invention, is schematically illustrated in FIG. 1 of the drawings.

Referring to FIG. 1, a donor 10 is connected into an extracorporeal circulation system as shown. Whole blood 12 is withdrawn from the donor 10 and circulated through a plasma separator 14, wherein it is separated into a plasma fraction 16 and a corpuscular element fraction 18. The separated plasma fraction 16 is then circulated through a plasma desalter 20, which in its preferred embodiment is an electrodialyzer, and wherein the plasma fraction 16 is subjected to a desalting treatment controlled so as to reduce the physiological salt content thereof to a predetermined level at which selected plasma proteins will preferentially precipitate. Upon exiting from the plasma desalter 20, the desalted plasma 22 is optionally infused with one or both of a precipitation-enhancing concentration of a heavy metal ion-containing solution 24 from a heavy metal ion infuser 26, and a pH-adjusting amount of an alkali or acid solution 28 from an alkali or acid infuser 30. The desalted plasma 22 is then passed through a precipitate separator 32, such as a centrifuge or filter, which effects a separation of the precipitated protein fraction 34 from the supernatant protein-impoverished desalted plasma fraction 36. The protein-impoverished desalted plasma fraction 36, a portion of which is optionally recycled back through the plasma desalter 20, is then circulated through a salt balance reconstitutor 38, which in its preferred embodiment is a passive dialyzer, and wherein the salt balance of the protein-impoverished desalted plasma fraction is reconstituted back to a physiological level. The resulting salt-reconstituted protein-impoverished plasma fraction 40 is thereafter recombined with the corpuscular element fraction 18 circulating from the plasma separator 14, and the thus-recombined fractions 42 are then returned back into the bloodstream of the donor 10.

The invention is further illustrated by way of the following examples.

EXAMPLE 1

This example illustrates the use of an electro-dialytic desalting treatment in combination with zinc chloride as a precipitating agent for milk whey proteins. It also documents that less zinc and less alkali are necessary to cause comparable precipitations in desalted whey than in normal whey.

The whey used in this experiment was the so-called sweet whey, prepared by the use of rennin. It was prepared in the customary manner starting with skim milk and using the Junket brank of rennin. The clotted casein was removed by filtration through cheese cloth and the whey so-obtained had a pH of 6.2.

Starting with this whey, two batches of desalted whey were prepared. One batch was prepared by recirculating-continuous flow electrodialysis, as explained earlier, and had a specific resistance of 2,000 ohm-cm, pH 4.3. The second batch was prepared by batch electrodialysis to a specific resistance of 20,000 ohm-cm, pH 4.4. Batch electrodialysis is amenable to more thorough desalting than recirculating-continuous electrodialysis. The low pH values are due to removal of buffering ions, the desalted protein solutions tending to assume the pH corresponding to the isoelectric point of the proteins. In both cases, negligible protein precipitation occurred as a result of the desalting treatment alone.

Preliminary experiments have shown that zinc chloride causes optimal precipitation of proteins in the pH range 6.5–8, whether in desalted solutions or saline solutions. Table I lists the conditions of 9 experiments, conducted on 100 ml aliquots of the non-desalted original whey or the two batches of desalted whey. The 0.5 M zinc chloride solution was infused slowly into the non-desalted whey, to avoid local concentration build-up which could cause excess protein precipitation. In the desalted samples, the zinc chloride could be added rapidly, as the low pH of desalted samples prevents formation of precipitates. The 0.1 M sodium hydroxide solution was infused slowly in all instances. The zinc molarity was calculated taking into account the dilution of the sample due to addition of the precipitating reagents. The residual protein concentration was estimated by spectrophotometric measurements at 280 nm. The last column indicates the percentage protein removed by the zinc precipitation, based on the measurement of residual protein and the dilution of the sample.

TABLE I

EFFECT OF ZINC IONS ON PROTEIN PRECIPITATION IN NORMAL AND DESALTED WHEY

| Exp. # | Whey Sample (100 ml each) | $ZnCl_2$ Added (ml of 0.5M) | NaOH Added (ml of 0.1M) | Zn Molarity (mM) | pH | Protein Removed (% of original) |
|---|---|---|---|---|---|---|
| 1 | non-desalted | 10 | 27 | 36.5 | 6.1 | 34 |
| 2 | non-desalted | 10 | 30 | 35.7 | 7.0 | 56 |
| 3 | desalted, 2000 ohm-cm | 1.5 | 13.5 | 6.5 | 7.0 | 77 |

TABLE I-continued
EFFECT OF ZINC IONS ON PROTEIN PRECIPITATION IN NORMAL AND DESALTED WHEY

| Exp. # | Whey Sample (100 ml each) | ZnCl₂ Added (ml of 0.5M) | NaOH Added (ml of 0.1M) | Zn Molarity (mM) | pH | Protein Removed (% of original) |
|---|---|---|---|---|---|---|
| 4 | desalted, 2000 ohm-cm | 2.5 | 15 | 10.6 | 7.0 | 92 |
| 5 | desalted, 2000 ohm-cm | 2.5 | 16.5 | 10.5 | 7.3 | 95 |
| 6 | desalted, 2000 ohm-cm | 5 | 15.5 | 20.7 | 7.0 | 94 |
| 7 | desalted, 2000 ohm-cm | 5 | 18.5 | 20.2 | 7.4 | 100 |
| 8 | desalted, 20000 ohm-cm | 1.5 | 7 | 6.9 | 6.7 | 98 |
| 9 | desalted, 20000 ohm-cm | 1.5 | 7.5 | 7.0 | 7.0 | 100 |

The data reported in Table I show:

(1) At comparable zinc concentrations, precipitation is more complete if the solutions are brought to pH 7 or higher, than at lower pH values. This holds true for all three whey solutions.

(2) The amount of zinc ions needed to cause complete or near complete precipitation of all milk whey proteins is radically reduced by prior desalting of the whey. Thus, 7 mM zinc is sufficient to cause total protein precipitation in thoroughly desalted whey (Exp. 8 and 9), about 20 mM zinc is needed to completely precipitate the proteins in partially desalted whey (Exp. 7), and 36 mM zinc is still insufficient to cause complete protein precipitation in non-desalted whey (Exp. 2). In subsequent experiments, not reported in the above Table, complete protein precipitation from non-desalted whey was obtained at 43–60 mM zinc concentration.

(3) There are also significant savings in the amounts of alkali needed to adjust the pH to the pH region of optimal protein precipitation: 30 ml of 0.1 M NaOH in non-desalted whey, about 15 ml in partially desalted whey, and only 7.5 ml in thoroughly desalted whey. It should be pointed out that if acid whey, instead of sweet whey, would have been used for this separation, the savings in alkali would have been even more pronounced.

EXAMPLE 2

This example illustrates how the process described in Example 1 can be used to purify the proteins and carbohydrates of milk whey, while recovering the alkali and zinc used in the process.

The conditions of experiment 9, Table I, were used to process 1 liter of whey. It was first batch desalted to a specific resistance of above 25,000 ohm-cm and then added with 15 ml of 0.5 M zinc chloride. The pH was then adjusted to pH 7 by the addition of 80 ml of 0.1 M NaOH. The precipitated protein was centrifuged, resuspended in 200 ml of distilled water and solubilized by the addition of alkali, to pH 9. This solubilized protein was submitted to a second electrodialysis, which was continued until the protein solution again reached a specific resistance of above 25,000 ohm-cm. The final volume of the protein solution was adjusted to 250 ml, and the pH was 4.5, the protein concentration being 2.5%.

The supernatant obtained after centrifugation of the precipitated whey was also submitted to electrodialysis. After thorough desalting to a resistance of above 25,000 ohm-cm, the concentration of lactose in the deashed fluid was found to be 3.9%, and was protein-free (as determined by addition of trichloroacetic acid and heating). The analysis of zinc in the concentrating brine of the electrodialysis apparatus, after both treatments (of the precipitated protein and the supernatant) showed a recovery of 92% of the added zinc. The alkali recovery was 87%, as determined by titration.

The zinc concentration in the final protein solution was found to be 25 ugm/ml, and in the lactose solution the zinc concentration was 18 ugm/ml. All zinc analyses were carried out by atomic adsorption spectrometry.

It should be pointed out that the zinc precipitated proteins can be solubilized not only by the addition of alkali, as in the above example, but also by the addition of acid, for example, lactic acid, or by the addition of a zinc-binding chelating agent, such as ethylenediaminetetraacetic acid (EDTA). The precipitated proteins become solubilized above pH 8.5 and below pH 6, approximately. In either case, the solubilized protein solution can be deashed by electrodialysis, thereby removing the bulk of zinc ions added and preventing further precipitation. The solution can further be stabilized against precipitation of euglobulins by the addition of neutral salts, such as sodium chloride.

EXAMPLE 3

This example illustrates the use of an electrodialytic desalting treatment in combination with zinc chloride as a precipitating agent in the fractionation of human plasma to obtain an immunoglobulin-rich fraction as the precipitate and an immunoglobulin-impoverished albumin-rich fraction as the supernatant.

The source of this plasma was a patient with myastenia gravis, who was plasmaphoresed by conventional means. Aliquots of the plasma (40 ml each) were first electrodialyzed in the recycling mode to a specific resistance of over 50,000 ohm-cm and then slowly infused with 0, 0.8, 1.0, and 1.2 ml of 0.1 M zinc chloride solution. This corresponded to a concentration of 0, 2, 2.5, and 3 mM of zinc in the treated plasma aliquots. After the addition of zinc, all suspensions were brought to pH 7 by the slow addition of 0.1 M sodium hydroxide. Electrodialysis alone caused precipitation of some euglobulins, the precipitation increasing strikingly by the addition of zinc chloride and pH adjustment.

The precipitated proteins were removed by centrifugation. To prevent additional slow precipitation of proteins from the supernatant, i.e., to stabilize the supernatant against time-dependent further precipitation, each aliquot was added with 4 ml of 10x concentrated phosphate buffered saline (PBS). The precipitates were readily suspended in 20 ml PBS.

The concentration of the immunoglobulins IgG, IgM, and IgA, as well as of albumin were determined using commercial radial immunodiffusion plates (purchased from Kallestad Laboratories, Chaska, Minn.). The data on the centrifuged plasma supernatants are reproduced in Table II.

TABLE II

EFFECT OF ZINC IONS ON PROTEIN PRECIPITATION IN DESALTED HUMAN PLAZMA (DESALTING PRIOR TO ZINC ION ADDITION)

| Zinc molarity | IgG mg % | % | IgM mg % | % | IgA mg % | % | Albumin mg % | % |
|---|---|---|---|---|---|---|---|---|
| Initial plasma | (646) | (100) | (64) | (100) | (88) | (100) | (2700) | (100) |
| 0 mM | 505 | 78 | 28 | 44 | 69 | 78 | 2950 | 110 |
| 2 mM | 179 | 28 | 16 | 25 | 57 | 65 | 2410 | 91 |
| 2.5 mM | 135 | 21 | 14 | 22 | 54 | 61 | 2290 | 87 |
| 3 mM | 118 | 18 | 13 | 20 | 45 | 51 | 1960 | 75 |

The data show that electrodialysis alone, without the addition of zinc (0 mM zinc), causes only minimal removal of immunoglobulins IgG and IgA (reduced to 78% of original plasma value), the effect on IgM being more pronounced. Albumin remained intact, at least within the experimental error.

The last two lines of the table show that the addition of 2.5 or 3 mM zinc caused a greatly enhanced precipitation of all the immunoglobulins. Higher concentrations of zinc were not explored as even at the 3 mM zinc concentration, there was evidence that albumin began to precipitate in the process.

When additional aliquots of the plasma were similarly treated, but with the omission of the electrodialytic desalting treatment, zinc concentrations as high as 10 mM produced no appreciable protein precipitation.

When the centrifuged plasma supernatants were reelectrodialyzed for 30 minutes at 60 volts, complete removal of the zinc ions was obtained.

EXAMPLE 4

This example demonstrates the effect of reversing the sequence of steps in Example 3, i.e., carrying out the electrodialytic desalting subsequent to the zinc ion addition. The protocol followed was:

Step 1. Aliquots of 40 ml of plasma were placed in a beaker and slowly infused with 0, 0.8, 1.2, and 2 ml of 0.5 M zinc chloride solution using a motor-driven syringe and a magnetic stirrer. After the addition of zinc, 0.1 M sodium hydroxide was used to adjust the plasma to pH 7, this being the optimum pH for protein precipitation. The resulting zinc ion concentrations in the plasma were 0, 10, 15, 20, and 25 mM, respectively.

Step 2. The precipitated proteins were separated from the supernatant by centrifugation. One ml aliquots of the supernatant were saved for analysis and the precipitates were resuspended in 20 ml of phosphate buffered saline.

Step 3. All the supernatant plasmas from step 2 were electrodialyzed to a specific resistance of 50,000 ohm-cm, and the newly precipitated proteins were again removed by centrifugation. The precipitated proteins were again resuspended in 20 ml of phosphate buffered saline. The supernatants were titrated to pH 7, but this resulted in no significant further protein precipitation. Aliquots of the supernatants were again stabilized against further slow time-dependent protein precipitation by the addition of 10% of 10x concentrated phosphate buffered saline and saved for analysis.

All the solutions were submitted to the same analyses as reported in Example 3. The data on RID analysis of the immunoglobulins and albumin are reported in Table III. IgG data are reported on the supernatants from step 2 (prior to electrodialysis) and step 3 (after electrodialysis). No analyses on the supernatants from step 3 were carried out for IgM and IgA. Albumin was analyzed also after step 2, but no loss of albumin was registered and the data therefore omitted.

The following comments are in order: line 1 of Table III reports the initial plasma value, while line 2 reports the data obtained by electrodialysis alone, as no zinc was added. The addition of 10 mM zinc (line 3) does not cause any significant precipitation of IgG by itself, i.e., without electrodialysis (step 2), but shows a significant decrease (to 74%) following subsequent electrodialysis (step 3). With higher levels of zinc ions added (lines 4 to 6), in all instances the amount of IgG remaining in the supernatant was substantially decreased by the combined effect of zinc treatment and electrodialysis (step 3), as compared to the decrease observed on addition of zinc without subsequent electrodialysis (step 2).

TABLE III

EFFECT OF ZINC IONS ON PROTEIN PRECIPITATION IN DESALTED HUMAN PLASMA (DESALTING SUBSEQUENT TO ZINC ION ADDITION)

| | IgG | | | | IgM | | IgA | | Albumin | |
| | Step 2 | | Step 3 | | Step 2 | | Step 2 | | Step 3 | |
| Zinc molarity | mg % | % | mg % | % | mg % | % | mg % | % | mg % | % |
|---|---|---|---|---|---|---|---|---|---|---|
| Initial plasma | (646) | (100) | — | — | (64) | (100) | (88) | (100) | (2700) | (100) |
| 0 mM | — | — | 505 | 78 | — | — | — | — | 2950 | 110 |
| 10 mM | 675 | 104 | 478 | 74 | 53 | 83 | 73 | 83 | 2660 | 99 |
| 15 mM | 561 | 87 | 348 | 54 | 39 | 61 | 73 | 83 | 2400 | 89 |
| 20 mM | 268 | 42 | 207 | 32 | 32 | 50 | 73 | 83 | 2600 | 96 |
| 25 mM | 247 | 38 | 144 | 22 | 53 | 83 | 69 | 78 | 2600 | 96 |

EXAMPLE 5

This example illustrates the application of electrodialytic desalting to implement a selective plasmapheresis treatment in a dog afflicted with Myasthenia gravis and the beneficial effects derived from this treatment. The dog was a 40 lb male Queensland Blue Heeler. Prior to the plasmapheresis treatment, the dog was maintained on anticholinesterase drugs, yet had a loss of muscular coordination and was too weak to stand.

Blood access was gained through the cannulation of the dog's jugular veins and extracorporeal circulation was established. The dog was anticoagulated through administration of heparin and a continuous infusion of low levels of heparin was maintained throughout the procedure. The plasma was separated from the corpuscular elements by the use of the Aminco Celltrifuge (Trademark of the Aminco Corp., subsidiary of Baxter Laboratories). The dog's estimated plasma volume was 725 ml. A total of 597 ml of dog's plasma was electrodialyzed to a resistance of 10,700 ohm-cm and the precipitated euglobulin fraction removed by continuous filtration through an 8-plate filter press. The electrolyte contents of the desalted and clarified plasma was reconstituted by returning the plasma through a Cordis-Dow pediatric artificial kidney, using a balanced electrolyte solution as the dialyzate. The total amount of protein removed was 2.23 gm as measured by biuret, and it comprised 546 mg of immunoglobulin IgG, as determined by radial immunodiffusion.

There appeared to be a striking improvement in the muscular coordination of the dog following this first treatment, as he became able to stand. For this reason, the dog was submitted to a second treatment, 6 days later. The same procedure was employed, except that a total of 774 ml of plasma was treated, and the precipitated proteins were removed by centrifugation, using a continuous flow centrifuge manufactured by Haemonetics Corp. The analysis showed that 3.9 gm of total protein was removed, comprising 732 mg of IgG.

Samples of the dog's plasma were analyzed for titers of autoantibodies to acetylcholine receptors, said antibodies being believed to be the cause of the disease. The analysis of antigen binding capacity was as set forth in Table IV.

These data have demonstrated that significant amounts of antibodies were removed from the dog's circulation, even though there appeared to be a rebound in antibody levels following the first treatment. The clinical effects of the two treatments was striking: the dog recovered his muscular coordination, was able to stand freely, and the veterinarian in charge of the dog returned it to its owner. Anticholinesterase drug therapy could be discontinued. While it is known that myasthenia in dogs may be a self-limiting disease, the striking improvement of the dog immediately following the first as well as the second treatment was undoubtedly due to the removal of the autoantibodies from its circulation. This is consonant with the well known beneficial effects of conventional plasmapheresis in human patients with this disease.

TABLE IV

| Sample | Antigen Binding Capacity (nmol/liter) |
|---|---|
| Initial sample, first treatment | 0.14 |
| Treated sample, returned to the dog | 0.02 |
| Final sample, from dog on end of first treatment | 0.05 |
| Initial sample, second treatment | 0.20 |
| Treated sample, returned to the dog | 0.09 |
| Final sample, from dog on end of second treatment | 0.15 |

EXAMPLE 6

This example illustrates the application of electrodialytic desalting to implement a selective plasmapheresis treatment in a dog afflicted with multiple myeloma. This disease is known to cause an accumulation of immunoglobulin IgG to much higher than normal levels in the patient's circulating blood. The dog was a 45 lb female mongrel, with an estimated plasma volume of 900 ml. The electrophoretic pattern of the dog's initial plasma exhibited the characteristic IgG spike, diagnostic of multiple myeloma.

The procedure employed was similar to the one described in Example 5, and centrifugation was employed for the removal of precipitated plasma proteins. The plasma was desalted to a specific resistance of 95,000 ohm-cm which caused the precipitation of 77% of circulating IgG and 100% of circulating IgM. Precipitation was observed to have commenced at a specific resistance of only 800 ohm-cm. The electrophoretic pattern of the redisolved precipitate showed that the procedure resulted in the precipitation of preponderantly beta and gamma globulins. Some albumin was also evident in the pattern, due to the unavoidable occlusion of all plasma proteins in the voluminous precipitate. The electrophoretic pattern of the desalted and cleared plasma, returned to the dog, showed that the proportion of IgG had been reduced to near normal levels.

EXAMPLE 7

This example illustrates the use of zinc ions to cause increased precipitation of immunoglobulins in selective plasmapheresis by electrodialytic desalting. A normal dog was utilized as blood donor, and the procedure was the same as in Examples 5 and 6, centrifugation having been employed for the clearing of precipitated proteins from desalted plasma.

Two batches of 240 ml each of the dog's plasma were treated by electrodialytic desalting. In one of the batches, zinc chloride was added prior to desalting to a final concentration in plasma of 20 mM zinc, and in the other batch the zinc was added after desalting, its concentration being 3 mM and the pH was adjusted to pH 7. Both batches were desalted to a final specific electrical resistance of 35,000 ohm-cm.

The results of the two treatments are summarized in Table V. The electrophoretic patterns of the dog's initial plasma and plasma subjected to the above treatments document the preferential removal of beta and gamma globulins from the plasma.

TABLE V

| Sample | IgG decrease (%) | Albumin decrease (%) | Total protein removed (gm/100 ml) |
|---|---|---|---|
| Plasma, zinc added prior to desalting | 85 | 17 | 2.27 |
| Plasma, zinc added after desalting | 63 | 0 | 1.61 |

The embodiments of the invention in which an exclusive property or privilege is claimed are defined as follows:

1. A method for the fractionation of a proteinaceous solution or suspension mixture containing one or more salts selected from the group consisting of alkali metal salts and alkaline earth metal salts, comprising the steps of:
  (a) subjecting said proteinaceous mixture to a desalting treatment controlled so as to reduce said salt content thereof to a predetermined level;
  (b) incorporating into said proteinaceous mixture either prior or subsequent to step (a) a predetermined concentration of heavy metal ions, said predetermined level of salt content and said predetermined concentration of heavy metal ions each being selected and coordinated so that the combination thereof provides a synergistic precipitation of a protein fraction from the resulting heavy metal ion-containing desalted mixture; and (c) separating the precipitated protein fraction from the supernatant protein-impoverished mixture.

2. The method of claim 1, wherein step (b) includes an adjustment of the pH of said proteinaceous mixture to a value within the range which is optimal for the protein-precipitating action of the heavy metal ions employed.

3. The method of claim 1, wherein said heavy metal ions are selected from the group consisting of zinc, ferric, and ferrous ions.

4. The method of claim 1, wherein said heavy metal ions are zinc ions, and step (b) includes an adjustment of the pH of said proteinaceous mixture to a value within the range of from about 6.5 to about 8.

5. The method of claim 1, wherein said heavy metal ions are ferric ions, and step (b) includes an adjustment of the pH of said proteinaceous mixture to a value within the range of from about 4 to about 5.

6. The method of claim 1, wherein said predetermined level of salt content is a level at which the resulting desalted mixture exhibits a specific resistance greater than 300 ohm-cm.

7. The method of claim 1, wherein said predetermined level of salt content is a level at which the resulting desalted mixture exhibits a specific resistance greater than 10,000 ohm-cm.

8. The method of claim 1, wherein said desalting treatment is carried out by subjecting said proteinaceous mixture to electrodialysis.

9. The method of claim 1, wherein step (b) is carried out subsequent to step (a).

10. The method of claim 1, wherein subsequent to step (c) said heavy metal ions are recovered from one or both of said precipitated protein fraction and said supernatant mixture.

11. The method of claim 1, wherein said proteinaceous mixture is milk whey.

12. The method of claim 1, wherein said proteinaceous mixture is selected from the group consisting of blood plasma, serum, and fractions derived therefrom.

13. The method of either of claims 11 or 12, wherein said precipitated protein fraction separated in step (c) is an immunoglobulin-rich fraction, and said supernatant mixture is an immunoglobulin-impoverished albumin-rich fraction.

14. In a selective plasmapheresis method for the removal or recovery of one or more selected plasma proteins from whole blood, comprising the steps of withdrawing whole blood from a living donor, separating said whole blood into a plasma fraction and a corpuscular element fraction, treating said plasma fraction so as to remove said selected plasma proteins therefrom, recombining the resulting protein-impoverished plasma fraction with said corpuscular element fraction, and returning said recombined fractions back into the blood stream of said donor, the improvement wherein said protein-impoverished plasma fraction is obtained by the steps comprising:

(a) subjecting said separated plasma fraction to a desalting treatment controlled so as to reduce the physiological salt content thereof to a predetermined level at which said selected plasma proteins will preferentially precipitate;

(b) separating the precipitated protein fraction from the supernatant protein-impoverished desalted plasma fraction; and (c) reconstituting the salt balance of said protein-impoverished desalted plasma fraction back to a physiological level.

15. The method of claim 14, wherein said donor is a patient whose circulating blood contains said selected plasma proteins in a noxiously high concentration, and the procedure is carried out to an extent sufficient to provide a therapeutically effective removal of said selected plasma proteins from the patient's circulating blood.

16. The method of claim 14, wherein said selected plasma proteins are selected from the group consisting of immunoglobulins, macroglobulins, antibodies, antigen-antibody complexes, lipoproteins, and Factor VIII.

17. The method of claim 14, wherein said precipitated protein fraction separated in step (b) is an immunoglobulin-rich fraction, and said protein-impoverished plasma fraction is an immunoglobulin-impoverished albumin-rich fraction.

18. The method of claim 14, carried out as a continuous or semicontinuous flow selective plasmapheresis procedure wherein steps (a) through (c) are effected on-line while said blood and its plasma and corpuscular element fractions are maintained in extracorporeal circulation.

19. The method of claim 14, wherein said desalting treatment is carried out by subjecting said plasma fraction to electrodialysis.

20. The method of claim 14, wherein the salt balance reconstitution step is carried out by passive dialysis of said protein-impoverished desalted plasma fraction against a physiologically balanced electrolyte solution.

21. The method of claim 14, wherein the salt balance reconstitution step is carried out by the addition of a concentrated solution of suitably balanced electrolytes to said protein-impoverished desalted plasma fraction.

22. The method of claim 14, including the further step of incorporating into said plasma fraction in conjunction with its desalting relatively nontoxic heavy metal ions selected from the group consisting of zinc, ferric, and ferrous ions, in a concentration sufficient to enhance such preferential precipitation of said selected plasma proteins.

23. The method of claim 22, wherein said heavy metal ions are zinc ions, their incorporation into said plasma fraction is carried out subsequent to said desalting and is accompanied by an adjustment of the pH of said plasma fraction to a value within the range of from about 6.5 to about 8, and said concentration of zinc ions is in the range of from about 2.5 to about 4 mM.

24. The method of claim 22, wherein said heavy metal ions are zinc ions, their incorporation into said plasma fraction is carried out prior to said desalting, and said concentration of zinc ions is in the range of from about 15 to about 25 mM.

25. In a continuous or semicontinuous flow selective plasmapheresis apparatus including means for separating whole blood into a plasma fraction and a corpuscular element fraction, means for maintaining said blood and said fractions thereof in extracorporeal circulation, and on-line plasma treating means for effecting removal of one or more selected plasma proteins from said plasma fraction, the improvement wherein said plasma treating means comprises in combination:

(a) plasma desalting means controllable so as to effect a reduction in the physiological salt content of said plasma fraction to a predetermined level at which said selected plasma proteins will preferentially precipitate;

(b) means for separating the precipitated protein fraction from the supernatant protein-impoverished desalted plasma fraction; and (c) means for reconstituting the salt balance of said protein-impoverished desalted plasma fraction back to a physiological level.

26. The apparatus of claim 25, wherein said plasma desalting means comprises an electrodialyzer.

27. The apparatus of claim 25, wherein said precipitate separating means comprises a centrifuge or filter.

28. The apparatus of claim 25, wherein said salt balance reconstituting means comprises a passive dialyzer.

* * * * *

UNITED STATES PATENT AND TRADEMARK OFFICE
CERTIFICATE OF CORRECTION

PATENT NO. : 4,486,282
DATED : 22 February 1983
INVENTOR(S) : Milan Bier

It is certified that error appears in the above—identified patent and that said Letters Patent is hereby corrected as shown below:

Column 2, line 56, delete "withdrawm", and insert --withdrawn--

Signed and Sealed this

Twenty-first Day of May 1985

[SEAL]

Attest:

DONALD J. QUIGG

Attesting Officer     Acting Commissioner of Patents and Trademarks